(12) United States Patent
Burghardt et al.

(10) Patent No.: US 8,743,359 B2
(45) Date of Patent: Jun. 3, 2014

(54) OPTICAL SURVEILLANCE OF MIXING AND SEPARATION

(75) Inventors: Geza Burghardt, Rotkreuz (CH); Pirow Engelbrecht, Royston (GB); Andreas Gisler, Thalwil (CH); Nicholas Hastings, Fen Drayton (GB); Rolf Schneebeli, Mettmenstetten (CH); David Roger Tegerdine, Royston (GB)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 13/157,725

(22) Filed: Jun. 10, 2011

(65) Prior Publication Data

US 2012/0287434 A1 Nov. 15, 2012

(30) Foreign Application Priority Data

Jun. 15, 2010 (EP) .................................... 10165996

(51) Int. Cl.
*G01N 15/02* (2006.01)
*G01N 33/543* (2006.01)
*G01N 35/00* (2006.01)

(52) U.S. Cl.
CPC ...... *G01N 35/0098* (2013.01); *G01N 33/54326* (2013.01)
USPC ........... 356/335; 356/336; 356/337; 356/246; 436/526; 436/528

(58) Field of Classification Search
USPC ......... 356/335–343, 246, 432–444, 311, 417, 356/526, 628; 435/7.1, 286.5, 289.1, 288.4; 436/524, 518, 536; 422/100, 99, 101, 422/186.01
See application file for complete search history.

(56) References Cited

U.S. PATENT DOCUMENTS

| | | | |
|---|---|---|---|
| 4,004,150 A | 1/1977 | Natelson | |
| 4,452,902 A | 6/1984 | Suovaniemi et al. | |
| 5,698,450 A * | 12/1997 | Ringrose et al. | 436/526 |
| 5,981,202 A * | 11/1999 | Masuko | 435/7.9 |
| 6,043,880 A * | 3/2000 | Andrews et al. | 356/311 |
| 6,238,911 B1 * | 5/2001 | Kasahara | 435/288.4 |
| 6,409,925 B1 * | 6/2002 | Gombinsky et al. | 210/695 |
| 6,805,840 B1 * | 10/2004 | Tajima | 422/501 |
| 7,214,346 B2 * | 5/2007 | Harper et al. | 422/82.05 |
| 8,071,395 B2 * | 12/2011 | Davis et al. | 436/524 |
| 2004/0053322 A1 | 3/2004 | McDevitt et al. | |
| 2005/0206895 A1 * | 9/2005 | Salmelainen | 356/318 |
| 2007/0172390 A1 * | 7/2007 | Ootani et al. | 422/64 |
| 2009/0117004 A1 * | 5/2009 | Fritchie et al. | 422/63 |
| 2009/0297327 A1 * | 12/2009 | Zobel et al. | 414/806 |
| 2010/0200405 A1 * | 8/2010 | Lenz | 204/600 |
| 2012/0019828 A1 * | 1/2012 | McCaffrey et al. | 356/432 |

FOREIGN PATENT DOCUMENTS

| | | |
|---|---|---|
| EP | 0691541 A2 | 1/1996 |
| EP | 0691541 A3 | 4/1996 |
| EP | 0691541 B1 | 4/2002 |
| JP | 9257796 A | 10/1997 |
| JP | 2003315338 A | 11/2003 |

(Continued)

*Primary Examiner* — Sang Nguyen
(74) *Attorney, Agent, or Firm* — Olga Kay (57) ABSTRACT

The present invention relates to a non-invasive method for surveilling mixing and separation of a suspension in an analytical system using solid phase particles for separation of an analyte by measuring particle distribution with a camera attached to a pipetting device.

14 Claims, 10 Drawing Sheets

(56) References Cited

FOREIGN PATENT DOCUMENTS

| | | | |
|---|---|---|---|
| JP | 4043132 B2 | 2/2008 | |
| WO | 2008044311 A1 | 4/2008 | |
| WO | 2009037636 A1 | 3/2009 | |
| WO | 2009129415 A1 | 10/2009 | |

* cited by examiner

OPTICAL SURVEILLANCE OF MIXING AND SEPARATION

FIELD OF THE INVENTION

The present invention relates to surveillance of mixing and separation in an analytical system using a solid phase for separation of an analyte from a sample.

BACKGROUND OF THE INVENTION

In analytical methods and systems isolation and separation of analytes is often required for efficient analysis. One method of isolating and separating an analyte comprises binding to magnetic or magnetizable particles in suspension, followed by separation in a magnetic field. The quality of the isolation and separation steps is dependent on appropriate particle distribution during binding, separation, and washing. Invasive methods are commonly used (e.g. placing a sensor in the separation vessel).

JP 2002 315 338 discloses measuring the properties of a liquid comprising magnetic particles in the presence of a magnetic filed, i.e. when the magnetic particles are attached to the side walls and are outside of the optical path.

WO2009/129415 discloses examples of detectors in integrated flow systems for analyte quantification. It does not disclose any specific arrangement of light source and detector. It also does not disclose any measuring of solid phase particle distribution during mixing and separation.

The present invention provides an improved method and system for surveilling mixing and separation using magnetic particles in an analytical system.

SUMMARY OF THE INVENTION

The present invention relates to a method of surveilling mixing and separation of a suspension comprising solid phase particles, comprising the steps of
  mixing or separating a suspension comprising solid phase particles from a liquid in a vessel
  illuminating said vessel with a light source;
  detecting light illuminated by said light source with said detecting device, wherein said detecting device is positioned above said vessel
  wherein the detected light is a measure of the particle distribution of solid phase particles present in said liquid.
This method has the advantage of allowing non-invasive surveillance of mixing and separation.

SHORT DESCRIPTION OF FIGURES

FIG. 2 a) shows a separation station with LED prints and magnets, and b) a heating station with an LED print.

FIG. 4 a) shows a perspective view of the first and second types of pipette tips. B) shows a pipette needle.

FIG. 18 a) to d) show different views of the second embodiment of the magnetic separation station.

DETAILED DESCRIPTION OF THE INVENTION

The present invention relates to a method of surveilling mixing and separation of a suspension comprising solid phase particles, comprising the steps of
  mixing or separating a suspension comprising solid phase particles from a liquid in a vessel
  illuminating said vessel with a light source;
  detecting light illuminated by said light source with said detecting device, wherein said detecting device is positioned above said vessel
  wherein the detected light is a measure of the particle distribution of solid phase particles present in said liquid.
Preferably, said detecting device is a CCD.

In some embodiments, the light source is located on the side or below said vessel, more preferably below said vessel.

In some embodiments, the detecting device is mounted movably, and said detecting device is moved and positioned over said vessel. In some embodiments, said detection device is mounted on a pipetting unit.

In one embodiment of the invention hereinbefore and hereinafter described, the detecting of light comprises acquiring images of the illuminated light.

From these images of light, particle distribution is measured and calculated by a control unit. The measurement is based on the reduced amount of light passing the liquid in the presence of solid phase particles.

In one aspect of the invention said acquired images are processed by said control unit, using a data reduction method. In some embodiments, the data reduction method comprises processing algorithms, for example, algorithms may comprise histograms or cross correlation. Other types of algorithms suitable for data reduction may also be used. Reduced image data are preferably generated by said data reduction. A discriminating algorithm preferably flags the test results according to the reduced image data.

The term "vessel" is understood to mean a single vessel or a single vessel in a multi-tube unit, a multiwell plate or a multi-tube unit or a well of a multiwell plate. For example, said vessel is comprised in a multiwell plate. Said multiwell plate may comprise vessels with a volume of at least 1 ml.

One embodiment of a multiwell plate is a process plate as described below. As is shown in the exemplary embodiments shown in the Figures, a vessel has an open top end and a closed bottom. The vessel is, thus, accessible to a pipet tip from the top.

The term "solid phase particles" as used herein relates to any type of solid support to which the analyte is capable of binding, either directly and non-specifically by adsorption, or indirectly and specifically. Indirect binding may be binding of an analyte to an antibody immobilized on the solid support, or binding of a tag to a tag binding compound, e.g. binding of 6×His tags to Ni-chelate. When the analyte is a nucleic acid, such indirect binding is preferably by binding to a capture nucleic acid probe which is homologous to a target sequence of the nucleic acid of interest. Thus, using capture probes attached on a solid support, a target analyte, preferably a target nucleic acid, can be separated from non-target material, preferably non-target nucleic acid. Such capture probe is immobilized on the solid support. Solid support material may be a polymer, or a composition of polymers. For example, solid phase particles can be magnetic or magnetizable particles. Preferred types of solid support material include magnetic silica particles, metal particles etc.

Non-specific binding of nucleic acid to silica particles may occur in the presence of chaotropic compounds. Such binding may also be referred to as direct binding, as opposed to the indirect binding described above. Preferably, the solid supports silica particles which comprise a magnetic or magnetizable material.

The term "magnetic" includes magnetic and magnetizable particles. More preferably, said solid phase particles are silica based particles, most preferably, magnetic glass particles. Such particles are well known in the art.

The terms, "mixing or separating" relates to any type of mixing and separating. Mixing preferably relates to mixing to allow binding of an analyte, preferably a nucleic acid, to a solid phase. Mixing may include shaking of the liquid suspension using a shaker. Mixing may also relate to sip & spit mixing, which comprises aspirating and dispensing the suspension with a pipette tip connected to a pipetting device. Sip & spit mixing is a preferred embodiment of mixing. Separating may include any method suitable for separating a solid phase with a bound analyte from liquid. One embodiment of separating comprises analyte bound to magnetic or magnetizable particles, preferably, magnetic or magnetizable silica particles, and separating using a magnetic separation station. Some embodiments of magnetic separation station and multiwell plate usable for magnetic separation are described hereinafter. Preferably, separating comprises removing the liquid from the solid phase, more preferably removing the liquid from the magnetic silica particles while applying a magnetic field in said magnetic separation station.

In some embodiments, said mixing comprises aspirating and dispensing with said pipette tip, and wherein said method additionally comprises the step of removing said pipette tips from said vessel following mixing.

The term "light source" relates to any type of light source that emits light that is detectable by a detecting device. Non-limiting examples of light sources are LEDs or halogen lamps.

Figures 4, 4B:
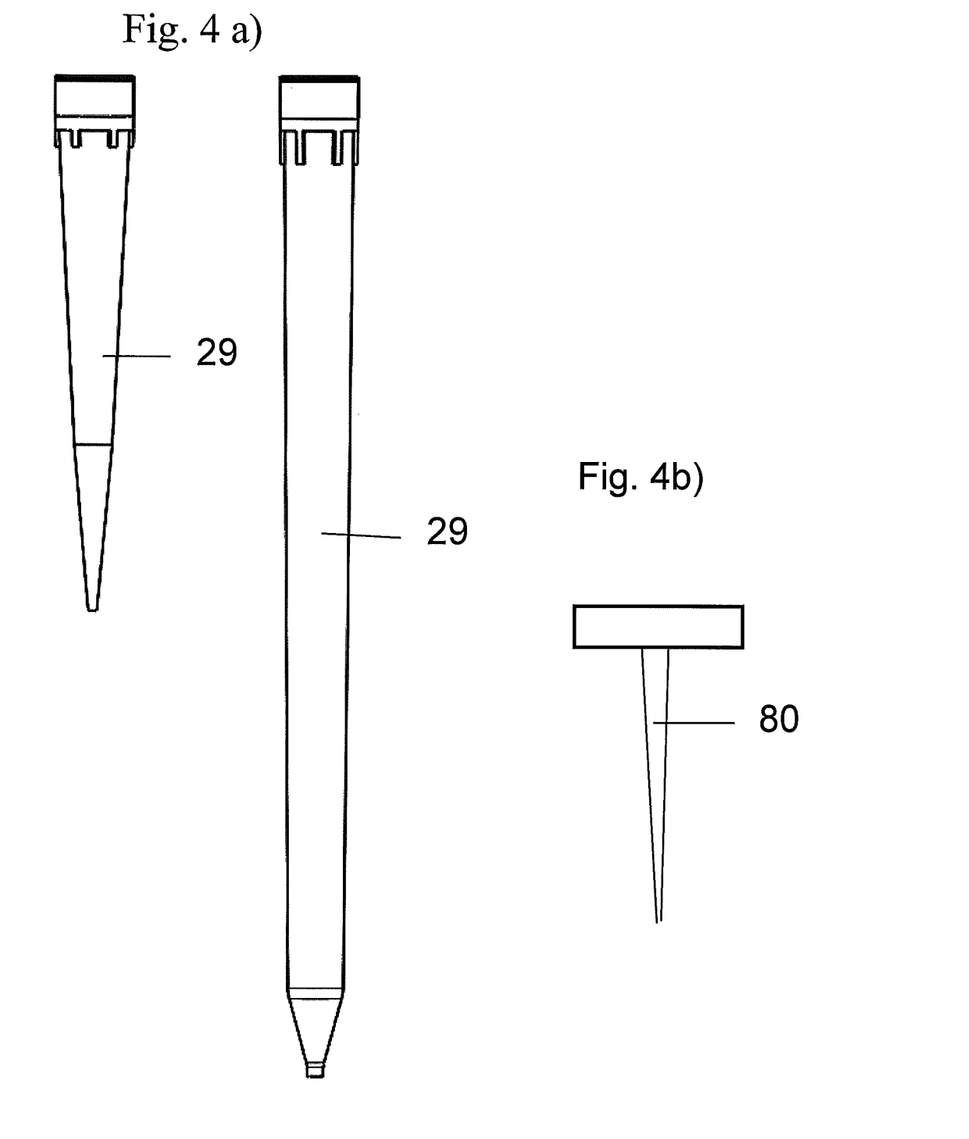

Non-limiting examples of pipette tips (29) and needles (80) are shown in FIG. 4 a) and b).

When surveillance of mixing is intended, particle distribution is measured by the detecting device, preferably the CCD when the pipette tips are removed from the vessels. This allows the control unit to identify vessels wherein the particle distribution is below a certain predefined threshold. Such vessels are then flagged by the control unit as invalid for the remaining analytical process.

In one embodiment, said separating comprises exposing said vessel to a magnetic field. More preferably, said separating comprises contacting said vessels with magnets of a separation station in a separation device. A preferred separation device of the present invention comprising a separation station and a multiwell plate is described below.

When surveillance of separation is intended, particle distribution may be measured by the detecting device when separation is terminated. This allows the identification of individual vessels containing liquid and magnetic particles, i.e. vessels in which separation was insufficient, by the control unit. These vessels and their content are then flagged by the control unit as invalid for the remainder of the analytical process.

Surveillance of mixing and separation according to the present invention allows the identification of individual tests as invalid if mixing or separation are erroneous, and, thus, improves data integrity and reliability of the results obtained by the analytical process.

In one aspect of the present invention, the surveillance of mixing and separation as described herein is comprised in a fully automated process for analysis of nucleic acids as described herein. Thus, any method, system instrument disclosed herein preferably comprises the method of surveillance of mixing and separation described herein. This leads to improved efficiency, precision and reliability of testing in said analytical method, system and instrument.

In one embodiment of the present invention, said vessel is integrally coupled to at least one further vessel.

In one aspect of the present invention, the detecting device is mounted above the vessel. Preferably, the detecting device is mounted on a housing. In another embodiment, the detecting device is mounted on the side of a pipetting unit.

The method of the present invention may be fully automated.

In one aspect of the present invention, a control unit identifies individual tests contained in the vessels which are invalid based on the measurement of said particle distribution.

The method of the present invention comprises acquiring of images, wherein said images are processed using a data reduction method, thereby obtaining reduced image data. Preferably, the data reduction method comprises processing algorithms. Non-limiting examples of such algorithms are histograms or cross correlation.

In one aspect of the present invention, a discriminating algorithm flags test results according to values of the reduced image data.

The present invention also relates to an analytical system comprising:

a separation station, wherein said separation station comprises a separation device comprising magnets which can be moved vertically, said separation device comprising light sources, at least one vessel, wherein said at least one vessel comprises magnetic or magnetizable particles in a liquid;

a pipetting unit for aspirating and dispensing said magnetic particles in said liquid;

a detecting device, preferably a CCD, wherein said detecting device is located above said vessel when the pipette tip is moved away from the vessel, wherein said light sources illuminate said vessels.

Preferably, the detecting device is mounted on the side of said pipetting unit.

The at least one vessels may comprise at least two vessels which are integrally formed. For example, said at least one vessels are comprised in a multiwell plate.

In one aspect of the present invention, said light sources are emitting light in a sideways or upwards direction, more preferably in an upwards direction. In one embodiment, said light sources are located below said at least one vessel, more preferably one of said light sources being located below any one of said vessels of said multiwell plate.

In one aspect of the present invention, the system additionally comprises a heating device, wherein said heating device comprises openings for receiving vessels: Preferably, said openings comprise LED on the bottom.

The analytical system of the present invention further preferably comprises a control unit for calculating the particle distribution of said magnetic particles in said liquid. More preferably, said control unit determines individual tests contained in said vessels which are invalid based on the measurement of the particle distribution by said detection device, preferably said CCD. Identification and flagging of tests with errors allows more reliable testing.

Other embodiments are as described hereinbefore.

Further embodiments, and features that are preferably comprised in the analytical system, are described below.

Figure 1:
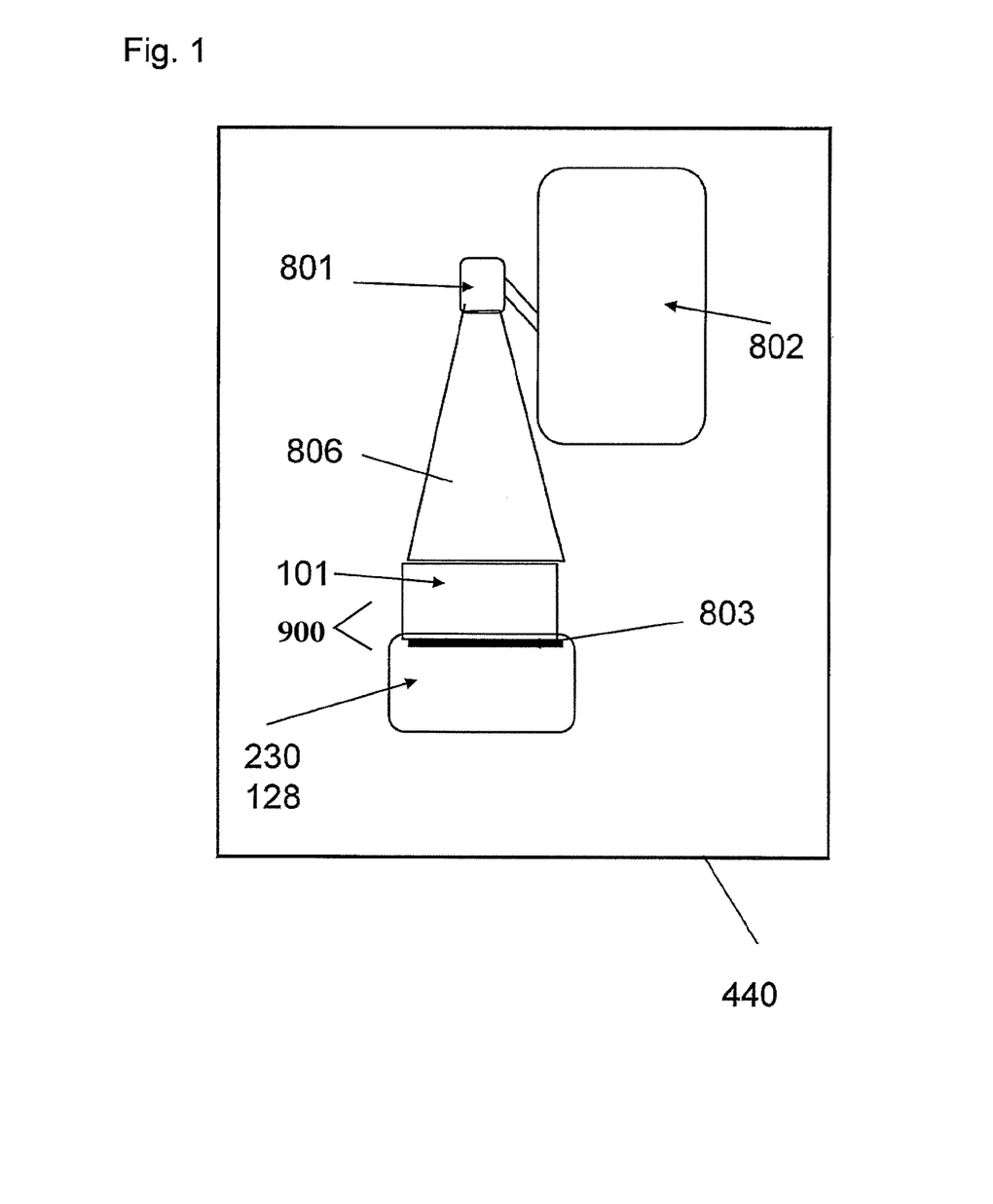
FIG. 1 shows a separation or heating station with LED print, and a camera attached to a process head for detecting light passing through the processing plate.
Figure 2:
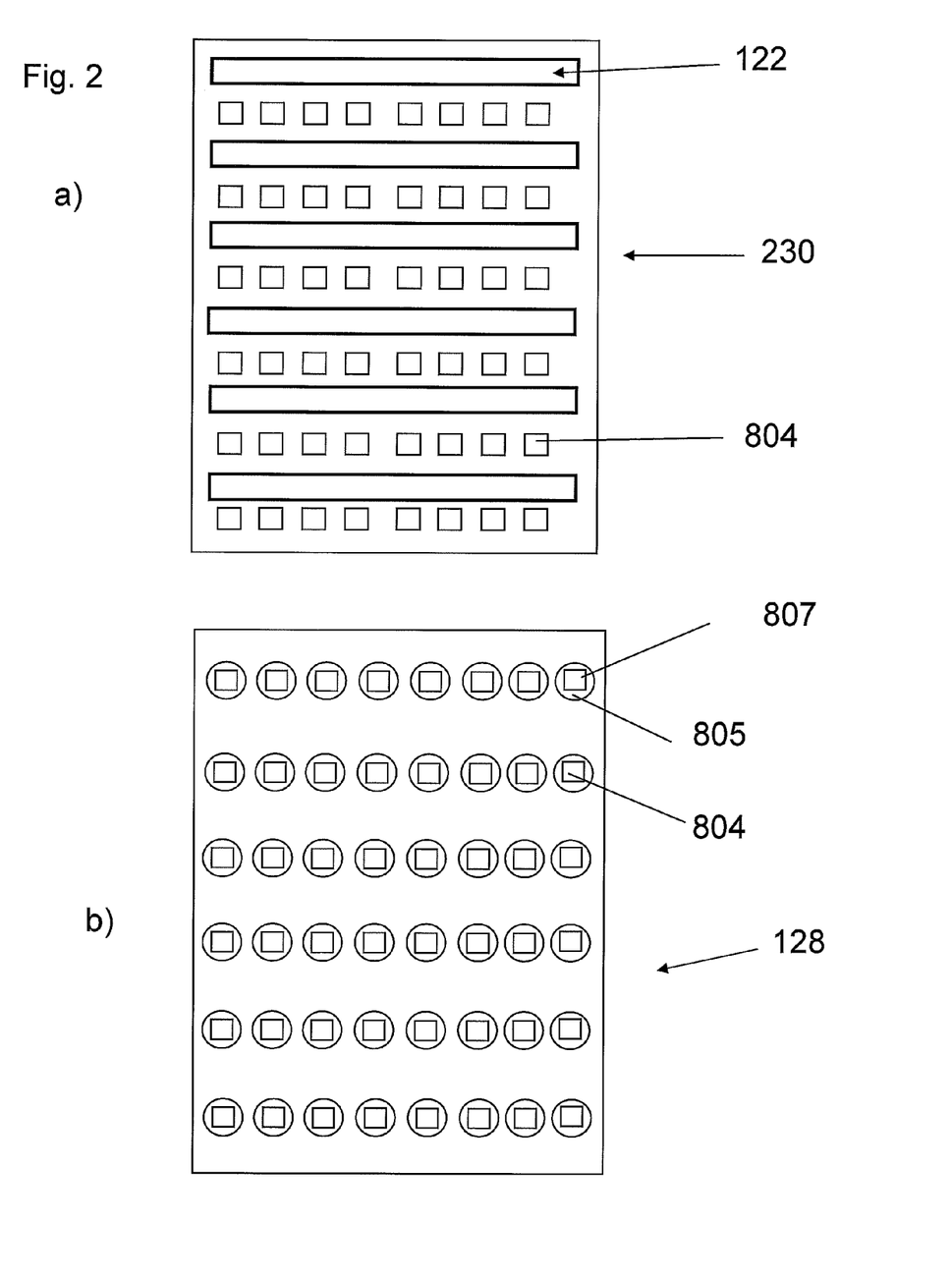
Figure 3:
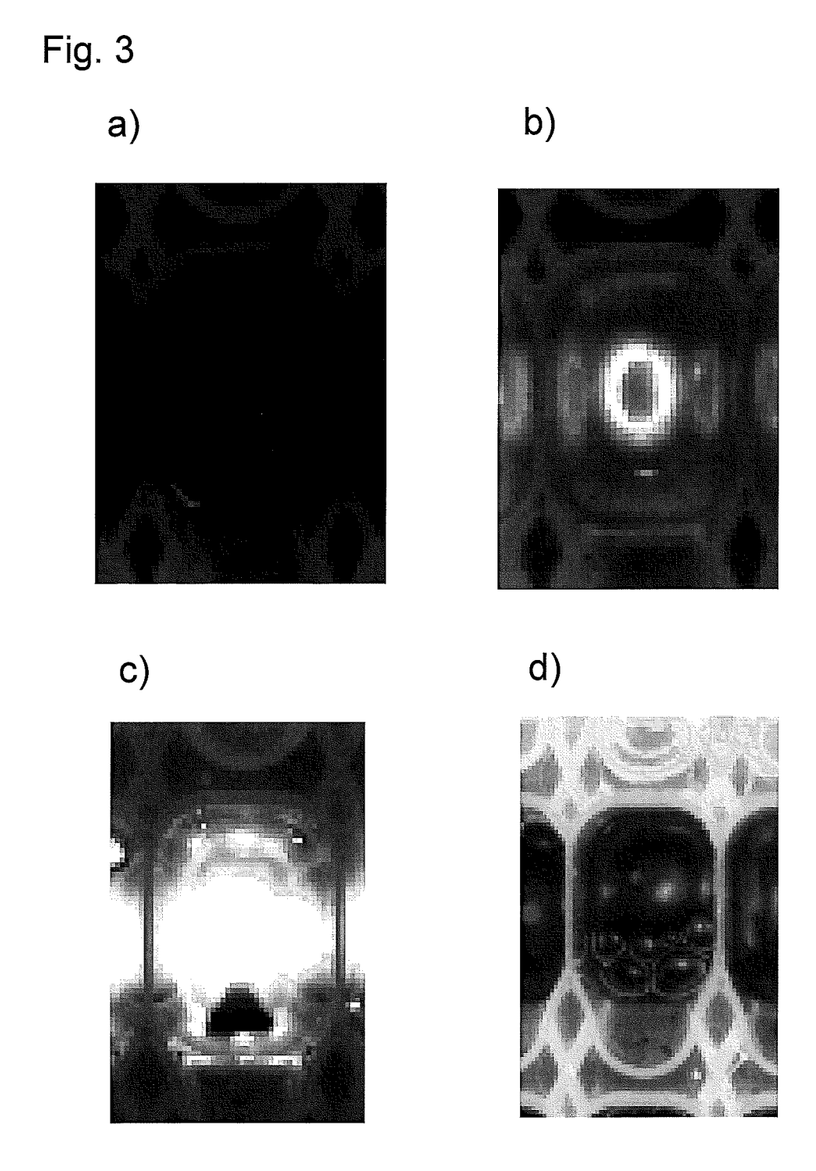
FIG. 3 shows vessels comprising a solid phase particles illuminated by LEDs. A) is a vessel with mixed solid phase particles; b) vessel with sedimented solid phase particles; c) particles in a vessel in a separated state (with magnetic field applied); d) vessel with solid phase particles in a "faulty" state.

One embodiment of an analytical system according to the present invention is shown in FIG. 1. A camera (801) is mounted on a pipetting device (802). The camera can capture (806) a multiwell plate (101). Preferred embodiments of the multiwell plate (101) are described hereinafter. A separation device (900) comprises the multiwell plate (101) and a separation station (230). The multiwell plate (101) is seated on a separation station (230) or heat block (128) which comprises an LED array (803). FIG. 2 schematically depicts a separation station (230) in a) with magnets (122) and LEDs (804). In b), a heating device (128) is shown with openings (805). The openings can receive vessels of the multiwell plate (101). On the bottom (807) of the openings (805), the LEDs (804) are located. FIG. 3 shows measurements of light emitted by the LEDs (804) located underneath the vessels of a multiwell plate (101) comprising magnetic particles as solid phase particles. In a), the magnetic particles are in a mixed state. The camera detects only low levels of light. In b) the particles are in a sedimented state. The camera detects light in areas without sedimented particles, and no light in areas with sedimented particles. In c) the magnetic particles are separated. The particles are sequestered at the wall of the vessel which is on the lower side of the picture. The camera detects light over the remaining area of the vessel which is now free of particles. In d) a "faulty" state is shown.

Analytical Apparatus and Method for Isolating and Analyzing an Analyte

The surveillance method described above is preferably used in a method for isolating and analyzing an analyte that may be present in a fluid sample. Said method comprises the automated steps of a) transferring said fluid sample from a sample vessel to a processing vessel with a pipette tip;
b) combining together a solid support material and said fluid sample in a well of said processing vessel for a period of time and under conditions sufficient to permit said analyte to be immobilized on the solid support material;
c) isolating the solid support material from other material present in the fluid sample in a separation station;
d) and purifying the analyte in the separation station by separating the fluid sample from the solid support material and washing the materials one or more times with a wash buffer.

Preferably, said pipette tip used in step a) is re-used after step a).

The term "receptacle" as used herein relates to a single vessel (or tube) or to a tube comprised in a multi-tube unit, or to a well (or vessel) of a multiwell plate.

In one embodiment, the reacting comprises generating a detectable signal and the method may additionally comprise the step of detecting a detectable signal.

The term "analyte" as used herein may be any type of biomolecule which is of interest for detection, and the detection thereof is indicative of a diagnostic status of an organism. The organism can be animal, including a human. Preferred analytes are proteins, polypeptides, antibodies or nucleic acids. More preferably, the analyte is a nucleic acid.

The term "reacting" as used herein relates to any type of chemical reaction of the analyte with reagents that is necessary to obtain a detectable signal. Preferably, said reacting comprises amplification. Amplification may be understood as any type of enhancement of a signal. Thus, amplification can be a conversion of a molecule by an enzyme, wherein said enzyme is coupled or bound to the analyte, leading to a detectable signal, wherein more signal molecules are formed than analyte molecules are present. One such non-limiting example is a formation of a chemiluminescent dye, e.g. using ECL. The term amplification further relates to nucleic acid amplification, if the analyte is a nucleic acid. This includes both linear, isothermal and exponential amplifications. Non-limiting examples of nucleic acid amplification methods are TMA, SDA, NASBA, PCR, including real-time PCR. Such methods are well known to the skilled person.

The term "solid support" as used herein relates to any type of solid support to which the analyte is capable of binding, either directly and non-specifically by adsorption, or indirectly and specifically. Indirect binding may be binding of an analyte to an antibody immobilized on the solid support, or binding of a tag to a tag binding compound, e.g. binding of 6× His tags to Ni-chelate. When the analyte is a nucleic acid, such indirect binding can occur by binding to a capture nucleic acid probe which is homologuous to a target sequence of the nucleic acid of interest. Thus, using capture probes attached on a solid support, a target analyte, for example a target nucleic acid, can be separated from non-target material, for example non-target nucleic acid. Such capture probe is immobilized on the solid support. Solid support material may be a polymer, or a composition of polymers. Other types of solid support material include magnetic silica particles, metal particles etc.

One type of non-specific binding of nucleic acid to silica particles occurs in the presence of chaotropic compounds. Such binding may also be referred to as direct binding, as opposed to the indirect binding described above. Preferably, the solid supports silica particles which comprise a magnetic or magnetizable material.

The analytical system of the present invention preferably comprises an automated analyzer for isolating and analyzing an analyte comprising a plurality of stations disposed within said analyzer. The plurality of stations comprises a sample dispensing station disposed in a first location. Said sample dispensing station may be constructed and arranged to dispense liquid sample comprising an analyte from a sample vessel to a processing vessel with pipette tips held in a rack. Further preferred sample dispensing stations are stations comprising a sample vessel, a processing vessel and a liquid dispensing unit. Said liquid dispensing unit is preferably a process device.

The automated analyzer further comprises a separation station disposed in a second location. Preferably, said separation station is constructed and arranged to receive said processing vessel holding said liquid sample and said rack holding pipette tips used in the sample dispensing station and to separate an analyte from other material present in the liquid sample. Another embodiment of a separation station is a separation station comprising movable magnets.

The automated analyzer further comprises a reaction station disposed in a third location, wherein said reaction station is constructed and arranged to analyze said analyte to obtain a detectable signal. Another embodiment of a reaction station is a station comprising an incubator. Said incubator may be a temperature-controlled incubator. Said incubator may be held at one constant temperature. Another embodiment of an incubator is a thermocycler block. A detector for detecting the detectable signal may be integrally connected to the reaction station. More preferably to the incubator as hereinbefore described. One type of detector comprises a nucleic acid quantification system for periodic measurement and quantification. The detector may additionally comprise a nucleic acid detection system which detects the signal and ascertains the presence or absence of the nucleic acid in the reaction receptacle based upon whether or not a signal above a threshold level is detected.

Alternatively, the automated analyzer additionally comprises a detecting station. The automated analyzer further comprises a transport mechanism. Said transport mechanism comprises a handler for handling consumables. Said handler preferably transports a consumable between stations. In one embodiment, said transport mechanism is constructed and arranged to transport said sample vessel and said rack from said sample dispensing station to said separation station. Further preferred embodiments of the automated analyzer of the present invention are individual or combined features disclosed herein.

In one embodiment of the analytical apparatus (400) hereinbefore described, said processing module (401) is a module for isolation and purification of an analyte. Therefore, the term "processing" as used herein is understood to relate to isolation and/or separation and/or capture and/or purification of an analyte. Said apparatus (400) may comprise a module for preparing samples for processing (402). Said apparatus (400) may comprise a module for amplification of said analyte (403). In one embodiment, said apparatus additionally comprises a module (404) for transferring amplification reagents from a storage receptacle to a receptacle comprising a purified analyte. Further embodiments of said apparatus are as hereinbefore and hereinafter described.

One embodiment of the automated analyzer (400) for use in performing a nucleic acid based amplification reaction comprises a plurality of modules (401, 402, 403). One module is a processing module disposed at a first location within the analyzer constructed and arranged to separate a nucleic acid from other material in a sample. Said processing module comprises a separation device as herein described. The analyzer further comprises an amplification module disposed and arranged at a second location within the analyzer. The amplification module comprises a temperature-controlled incubator for incubating the contents of at least one receptacle, preferably of a multiwell plate comprising the separated nucleic acid and one or more amplification reagents for producing an amplification product indicative of the target nucleic acid in the sample.

In one embodiment, the analytical system comprises a holding station and a multiwell plate set as described herein. Preferably, said multiwell plate set is fixed in said holding station. The multiwell plate may comprise a base with a rim which comprises recesses, wherein a positioning and fixing element, preferably a latch-clip (FIGS. 15 and 16), on said holding station contacts said recesses, wherein said contact exerts a downwards pressure on the base of the multiwell plate, thereby fixing the multiwell plate in the holding station. Further embodiments of the analytical system comprise individual or combined features described herein.

Figure 17:
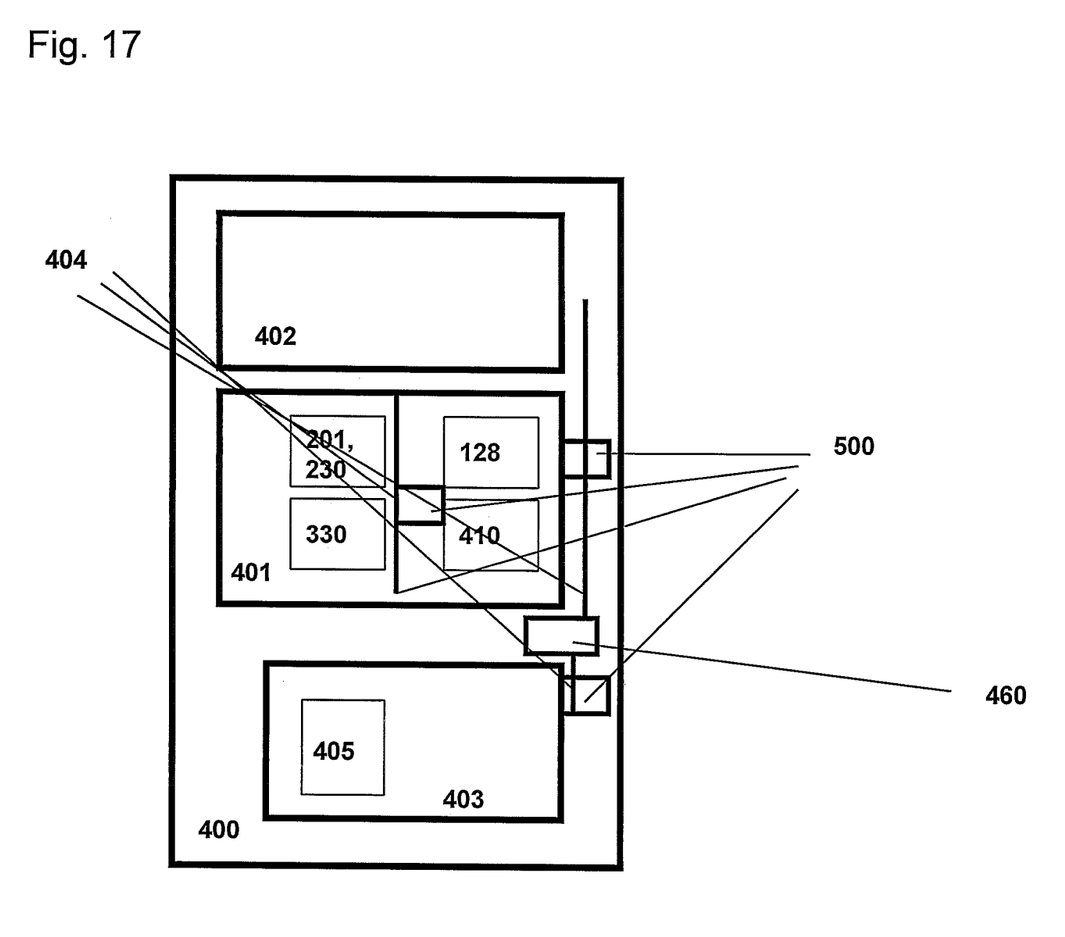
FIG. 17 shows schematic drawings of an analyzer comprising different stations, modules or cells.

The analytical instrument may additionally comprise a liquid handling module (404, 500). Further embodiments of the analytical instrument are described herein, either separately or as combinations of embodiments. One embodiment of an analyzer is shown in FIG. 17.

The analytical instrument according to the present invention preferably additionally comprises a sealing station (410). The sealing station (410) is preferably located in the process module (401).

The term "module" and "cell" are used interchangeably herein.

Multiwell Plate/Processing Plate

A multiwell plate comprises a multiwell plate for incubating or separating an analyte. Multiwell plates are preferably used in analytical systems. They allow parallel separation and analyzing or storage of multiple samples. Multiwell plates may be optimized for maximal liquid uptake, or for maximal heat transfer.

An improved multiwell plate for optimal use in an automated analytical system is provided by the present invention.

The multiwell plate is optimized for incubating or separating an analyte in an automated analyzer. Preferably, the multiwell plate is constructed and arranged to contact a magnetic device and/or a heating device.

Said multiwell plate comprises:
- a top surface comprising multiple vessels with openings at the top arranged in rows. The vessels comprise an upper part, a center part and a bottom part. The upper part is joined to the top surface of the multiwell plate and comprises two longer and two shorter sides. The center part has a substantially rectangular cross-section with two longer sides and two shorter sides;
- two opposing shorter and two opposing longer side walls and
- a base, wherein said base comprises an opening constructed and arranged to place the multiwell plate in contact with said magnetic device and/or a heating device.

In one embodiment of the multiwell plate, adjacent vessels within one row are joined on the longer side of said almost rectangular shape.

The multiwell plate may comprise a continuous space which is located between adjacent rows of vessels. Said continuous space is constructed and arranged to accommodate a plate-shaped magnetic device. In one embodiment, the bottom part of the vessels comprises a spherical bottom. In another embodiment, the bottom part of said vessels comprises a conical part located between said central part and said spherical bottom.

In one embodiment, the top surface comprises ribs, wherein said ribs surround the openings of the vessels. Preferably, one shorter side of said upper part of the vessels comprises a recess, said recess comprising a bent surface extending from the rib to the inside of the vessel.

Furthermore, in some embodiments, the vessels comprise a rounded inside shape.

For fixation to the processing or incubation stations, the base preferably comprises a rim comprising recesses. Latch clips on a station of an analyzer can engage with said recesses to fix the plate on a station.

In one embodiment, the vessels comprise an essentially constant wall thickness.

The processing plate (101) of the present invention is a 1-component plate. Its top surface (110) comprises multiple vessels (103) FIG. 7, FIG. 8). Each vessel has an opening (108) at the top and is closed at the bottom end (112). The top surface (110) comprises ribs (104) which are preferably elevated relative to the top surface (110) and surround the openings (108) of the vessels (103). This prevents contamination of the contents of the vessels (103) with droplets of liquid that may fall onto the top surface (110) of the plate (101). Views of the process plate are shown in FIGS. 5 to 16.

The footprint of the processing plate (101) preferably comprises a length and width of the base corresponding to ANSI SBS footprint format. More preferably, the length is 127.76 mm+/−0.25 mm, and the width is 85.48 mm+/−0.25 mm. Thus, the plate (101) has two opposing shorter side walls (109) and two opposing longer side walls (118). The processing plate (101) comprises form locking elements (106) for interacting with a handler (500). The processing plate (101) can be gripped, transported and positioned quickly and safely at high speed while maintaining the correct orientation and position. The form locking elements (106) for gripping may be located within the upper central part, preferably the upper central third of the processing plate (101). This has the advantage that a potential distortion of the processing plate (101) has only a minor effect on the form locking elements (106) and that the handling of the plate (101) is more robust.

Figure 14:
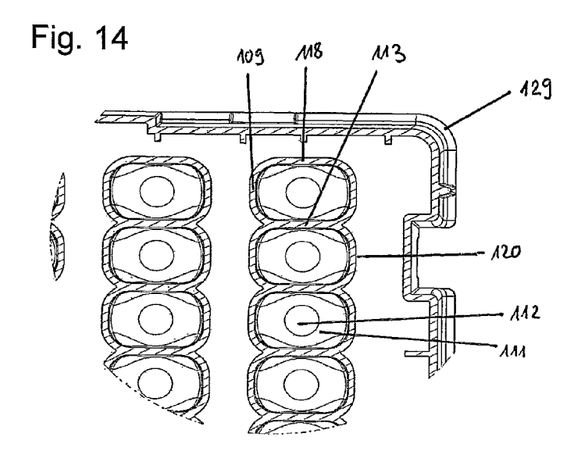
FIG. 14 shows a horizontal cross sectional view of the central region of the Processing plate and vessels.

The center part (120) of the vessels (103) has an almost rectangular cross section (FIG. 14). They are separated along the longer side (118) of the almost rectangular shape by a common wall (113) (FIG. 14). The row of vessels (103) formed thereby has the advantage that despite the limited space available, they have a large volume, preferably of 4 ml. Another advantage is that because of the essentially constant wall thickness, the production is very economical. A further advantage is that the vessels (103) strengthen each other and, thus, a high stability of the shape can be obtained.

Figures 11, 12, 13:
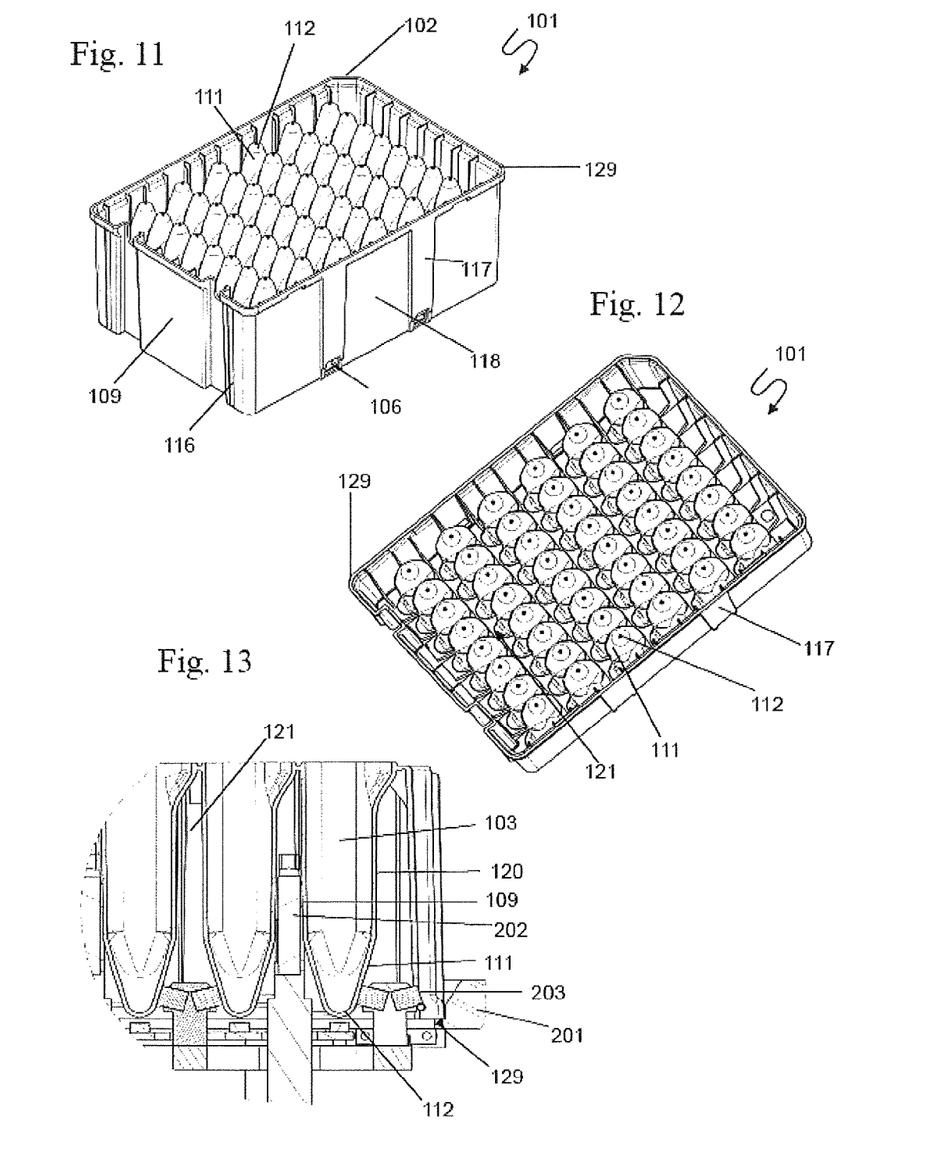
FIG. 11 shows a perspective view of the bottom of the Processing plate.
FIG. 12 shows a more vertical perspective view of the bottom of the Processing plate.
FIG. 13 shows the fitting of the smaller magnets of the first preferred embodiment of the separation station with the vessels of the Processing plate.

Between the rows (123) of vessels (103), a continuous space (121) is located (FIG. 11, FIG. 12). The space (121) can accommodate magnets (122) or heating devices 128) (FIG. 13). These magnets (122, 127) and heating devices (128) are preferably solid devices. Thus, magnetic particles (216) comprised in liquids (215) which can be held in the vessels (103) can be separated from the liquid (215) by exerting a magnetic field on the vessels (103) when the magnets (122, 127) are brought into proximity of the vessels (103). Or the contents of the vessels (103) can be incubated at an elevated, controlled temperature when the processing plate (101) is placed on the heating device (128). Since the magnets (122, 127) or heating devices (128) can be solid, a high energy density can be achieved. The almost rectangular shape of the central part (120) of the vessels (103) also optimizes the contact between the vessel wall (109) and a flat shaped magnet (122) or heating device (128) by optimizing the contact surface between vessel (103) and magnet (122) or heating device (128) and thus enhancing energy transfer into the vessel (103).

In the area of the conical bottom (111) of the vessels, the space (121) is even more pronounced and can accommodate further magnets (127). The combination of the large magnets (122) in the upper area and the smaller magnets (127) in the conical area of the vessels (3) allows separation of magnetic particles (216) in larger or small volumes of liquid (215). The small magnets (127), thus, make it easier to sequester the magnetic particles (216) during eluate pipetting. This makes it possible to pipette the eluate with minimal loss by reducing the dead volume of the magnetic particle (216) pellet. Furthermore, the presence of magnetic particles (216) in the transferred eluate is minimized.

Figures 5, 6, 7:
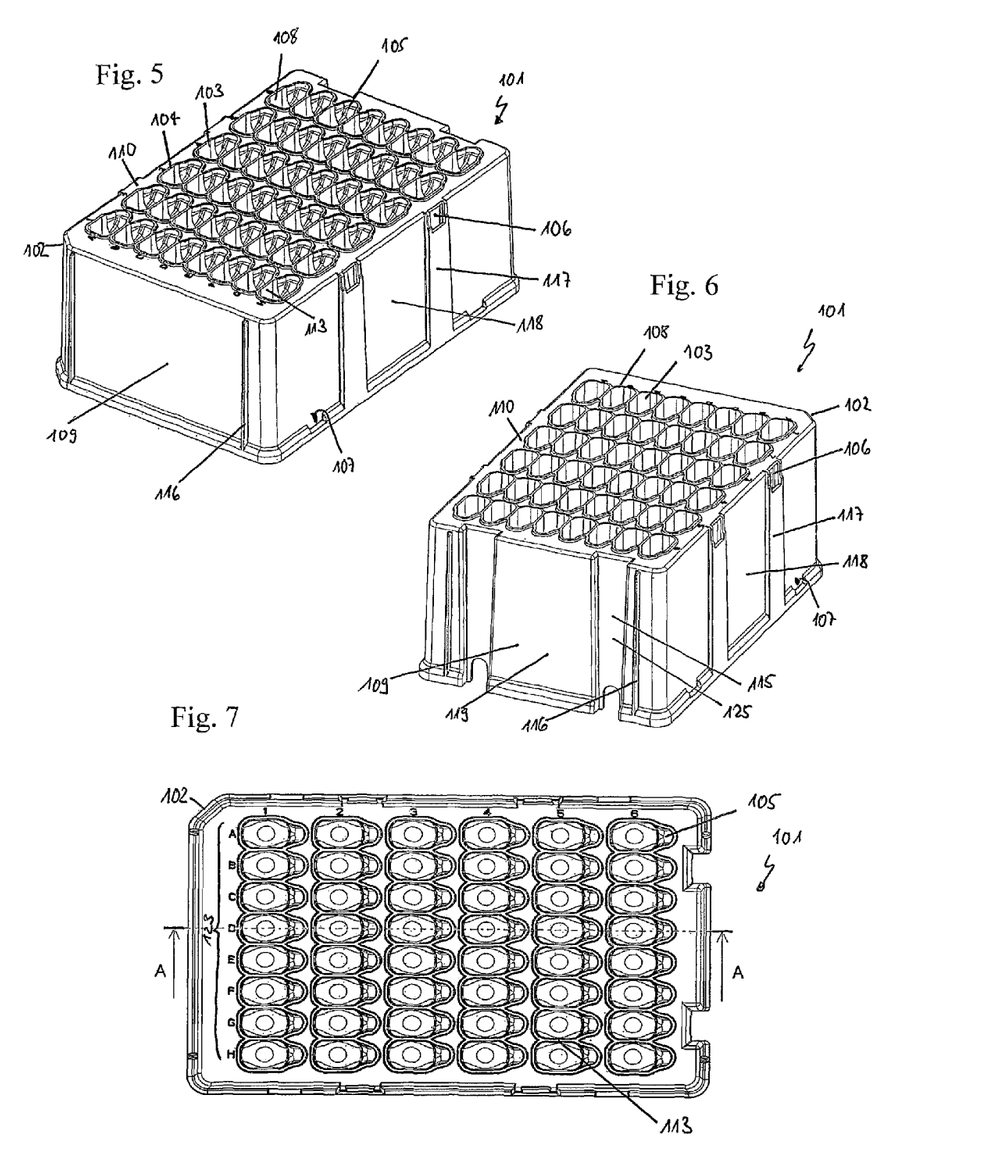
FIG. 5 shows a perspective view of the Processing Plate.
FIG. 6 shows a perspective view of the Processing Plate from the opposite angle.
FIG. 7 shows a top view of the processing plate.

At the upper end of the vessels (103), one of the shorter side walls (109) of the vessel (103) comprises an reagent inlet channel (105) which extends to the circumferential rib (104) (FIGS. 5 to 7). The reagents are pipetted onto the reagent inlet channel (105) and drain off the channel (105) into the vessel (103). Thus, contact between the pipette needle (80) or tip (3, 4) and liquid contained in the vessel is prevented. Furthermore, splashes resulting from liquid being directly dispensed into another liquid (215) contained in the vessels (103), which may cause contamination of the pipette needle (80) or tip (3, 4) or neighboring vessels (103) is prevented. Sequential pipetting onto the reagent inlet channel (105) of small volumes of reagents followed by the largest volume of another reagent ensures that the reagents which are only added in small amounts are drained completely into the vessel (103). Thus, pipetting of small volumes of reagents is possible without loss of accuracy of the test to be performed.

Figure 8:
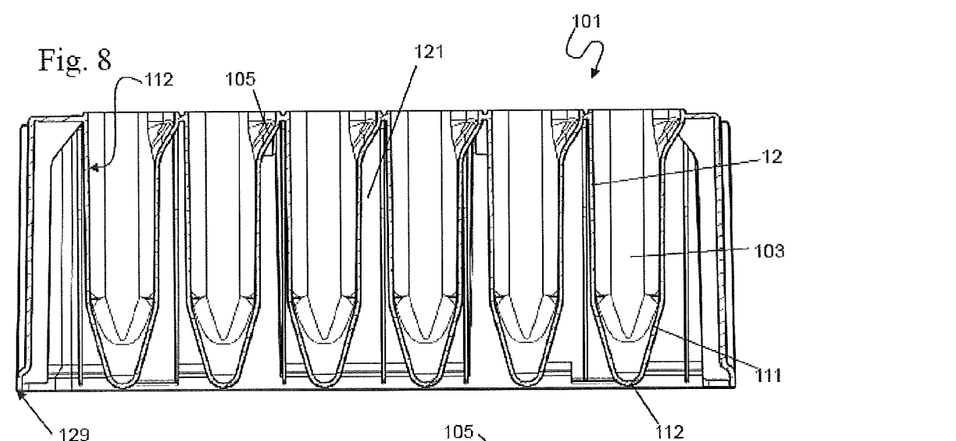
FIG. 8 shows a cross-sectional view along the longer side of the processing plate.

On the inside, on the bottom of the vessels (111, 112), the shape becomes conical (111) and ends with a spherical bottom (112) (FIG. 8). The inside shape of the vessel (114), including the rectangular center part (120), is rounded. The combination of spherical bottom (112), rounded inside shape (114), conical part (Ill) and refined surface of the vessels (103) leads to favorable fluidics which facilitate an effective separation and purification of analytes in the processing plate (101). The spherical bottom (112) allows an essentially complete use of the separated eluate and a reduction of dead-volume which reduces the carryover of reagents or sample cross-contamination.

Figures 9, 10:
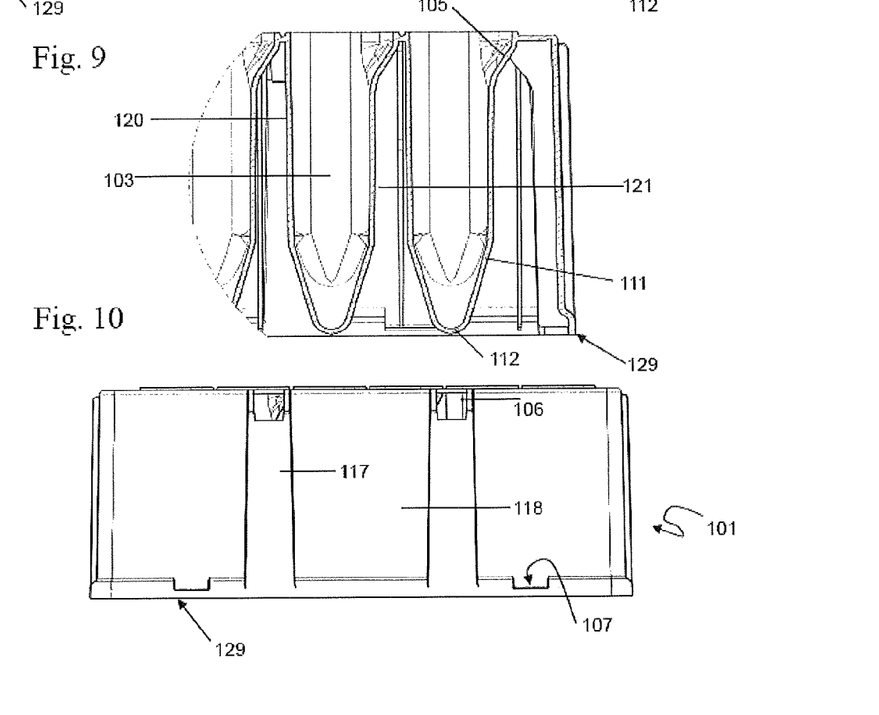
FIG. 9 shows a partial view of the cross-sectional view.
FIG. 10 shows a perspective view of the longer side of the Processing plate.
Figure 15:
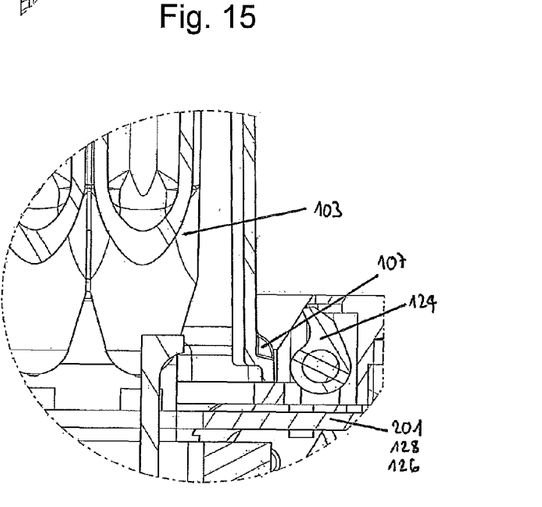
FIG. 15 shows the fitting of the Processing plate in a station for receiving the Processing plate (e.g. the magnetic separation station), with the locking mechanism disengaged.
Figure 16:
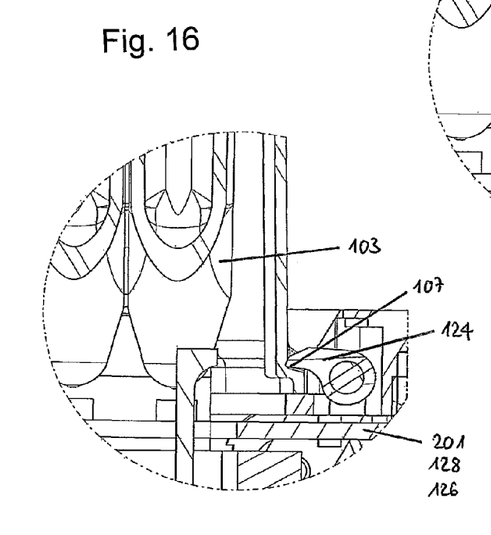
FIG. 16 shows the fitting of the Processing plate in a station for receiving the Processing plate (e.g. the magnetic separation station), with the locking mechanism engaged.

The rim on the base (129) of the processing plate (101) comprises recesses (107) for engagement with latch clips (124) on the processing station (201) or heating device (128) or analytical instrument (126) (FIG. 10, FIG. 15, FIG. 16). The engagement of the latch clips (124) with the recesses (107) allows positioning and fixation of the processing plate (101) on the processing station (201). The presence of the recesses (107) allows the latch force to act on the processing plate (101) almost vertically to the base (129). Thus, only small forces acting sideways can occur. This reduces the occurrence of strain, and, thus, the deformation of the processing plate (101). The vertical latch forces can also neutralize any deformations of the processing plate (101) leading to a more precise positioning of the spherical bottoms (111) within the processing station (201). In general, the precise interface between the processing plate (101) and the processing station (201) or heating device (128) within an analyzer (126) reduces dead-volumes and also reduces the risk of sample cross-contamination.

Separation Station

In one aspect of the present invention, a device for separating an analyte bound to magnetic particles in a liquid contained in a vessel is included. The device comprises a multiwell plate comprising vessels with an opening at the top surface of the multiwell plate and a closed bottom. The vessels comprise an upper part, a center part and a bottom part, wherein the upper part is joined to the top surface of the multiwell plate and preferably comprises two longer and two shorter sides. The center part has a substantially rectangular cross-section with two longer sides, wherein said vessels are aligned in rows. A continuous space is located between two adjacent rows for selectively contacting at least one magnet mounted on a fixture with the side walls in at least two Z-positions. The device further comprises a magnetic separation station comprising at least one fixture. The fixture comprises at least one magnet generating a magnetic field. A moving mechanism is present which vertically moves said at least one fixture comprising at least one magnet at least between first and second positions with respect to the vessels of the multiwell plate. Preferably, said at least two Z-positions of the vessels comprise the side walls and the bottom part of said vessels. The magnetic field of said at least one magnet preferably draws the magnetic particles to an inner surface of the vessel adjacent to said at least one magnet when said at least one magnet is in said first position. The effect of said magnetic field is less when said at least one magnet is in said second position than when said at least one magnet is in said first position. Preferably, the fixture comprising said at least one magnet comprises a frame. The vessels have preferred features as described under Multiwell plate/Processing plate. One such preferred feature is that at least a part of said vessels has a substantially rectangular cross-section orthogonal to the axis of said vessels.

In said first position, said at least one magnet is adjacent to said part of said vessels. Adjacent is understood to mean either in close proximity such as to exert a magnetic field on the contents of the vessel, or in physical contact with the vessel.

The separation station comprises a frame to receive the multiwell plate, and latch-clips to attach the multiwell plate. Preferably, the separation station comprises two types of magnets. This embodiment is further described below.

A second embodiment is described below, which comprises a spring which exerts a pressure on the frame comprising the magnets such that the magnets are pressed against the vessels of the multiwell plate.

The first magnets may be constructed and arranged to interact with vessels of a multiwell plate for exerting a magnetic field on a large volume of liquid comprising magnetic particles held in said vessels. Said second magnets preferably are constructed and arranged to interact with vessels of a multiwell plate for exerting a magnetic field on a small volume of liquid comprising magnetic particles held in said vessels. Said first and second magnets can be moved to different Z-positions.

The present invention further comprises a method of isolating and purifying an analyte, preferably a nucleic acid. The method comprises the steps of binding an analyte to magnetic particles in a vessel of a multi well plate. The vessel comprises an upper opening, a central part and a bottom part. The bound material is then separated from unbound material contained in a liquid when the major part of the liquid is located above the section where the conical part of the vessel is replaced by the central part with the rectangular shape, by moving a magnet from a second position to a first position and, in said first position, applying a magnetic field to the central part and, optionally, additionally applying a magnetic field to the bottom part of said vessel. The magnetic particles can optionally be washed with a washing solution. A small volume of liquid, wherein the major part of the liquid is located below the section where the conical part of the vessel is replaced by the central part with the rectangular shape is separated from said magnetic particles by selectively applying a magnetic field to the bottom part of said vessel.

The method hereinbefore described may additionally comprise between steps c) and d) the step of eluting said nucleic acid. The method may comprise the step of transferring said eluate from a said multiwell plate to a second multiwell plate. In another embodiment, in step b), a first type of magnet is moved from a second position to a first position to apply a magnetic field to a central part of the vessel, and, optionally, a second type of magnet is moved to the bottom part of the vessel to apply a magnetic field. Optionally, a magnet is moved to the central part of the vessel for step b), and the magnet is moved to the bottom part of said vessel into a third position for eluting said nucleic acid.

The present invention also relates to a magnetic separation station for separating an analyte bound to magnetic particles, said separation station comprising first magnets which are constructed and arranged to interact with vessels of a multiwell plate for exerting a magnetic field on a large volume of liquid comprising magnetic particles held in said vessels, and second magnets constructed and arranged to interact with vessels of a multiwell plate for exerting a magnetic field on a small volume of liquid comprising magnetic particles held in said vessels, and wherein said first and second magnets can be moved to different Z-positions. Some embodiments of the magnetic separation station are described herein.

In one embodiment, the separation station (230) comprises at least one fixture (231) comprising at least one magnet (232), preferably a number of magnets equal to a number of vessels (103) in a row (123). Preferably, the separation station (230) comprises a number of fixtures (231) equal to the number of rows (I 23) of the multiwell plate (101) hereinbefore described. For example, six fixtures (231) are mounted on the separation station (230). At least one magnet (232) is mounted on one fixture (231). Preferably, the number of magnets (232) equals the number of vessels (103) in one row (123). For example, eight magnets (232) are mounted on one fixture (231). One type of magnet (232) is comprised on said fixture (231). For example, the magnet (232) is mounted on one side which is oriented towards the vessels with which the magnet interacts.

The fixture (231) is mounted on a base (233). Optionally, said mount is flexible. The base (233) comprises springs (234) mounted thereon. The number of springs (234) is at least one spring per fixture (231) mounted on said base (233). The base further comprises a chamfer (236) which limits the movement of the spring and, consequently, the fixture (231) comprising the magnets (232). Any one of said springs (234) is constructed and arranged to interact with a fixture (231). More preferably, said spring (234) is a yoke spring. Said interaction controls the horizontal movement of the fixtures (231). Furthermore, the separation station (230) comprises a frame (235). The base (233) with fixtures (231) is connected to the frame (235) by a moving mechanism as described hereinbefore for the magnets (232) of the first embodiment.

Said base (233) and fixture (231) may be constructed and arranged to move vertically (in Z-direction).

The multiwell plate (10.1) hereinbefore described is inserted into the separation station (230). The fixture (231) comprising the magnets (232) is moved vertically. Any one fixture (232) is, thus, moved into a space (121) between two rows (123) of vessels (103). The vertical movement brings the magnets (232) mounted on a fixture (231) into contact with the vessels (103). The Z-position is chosen depending on the volume of liquid (215) inside the vessels (103). For large volumes, the magnets (232) contact the vessels (103) in a center position (120) where the vessels (103) are of an almost rectangular shape. For small volumes of liquid (215) where the major part of the liquid (215) is located below the center part (120) of the vessels (103), the magnets (232) preferably contact the conical part (111) of the vessels (103).

Figure 18:
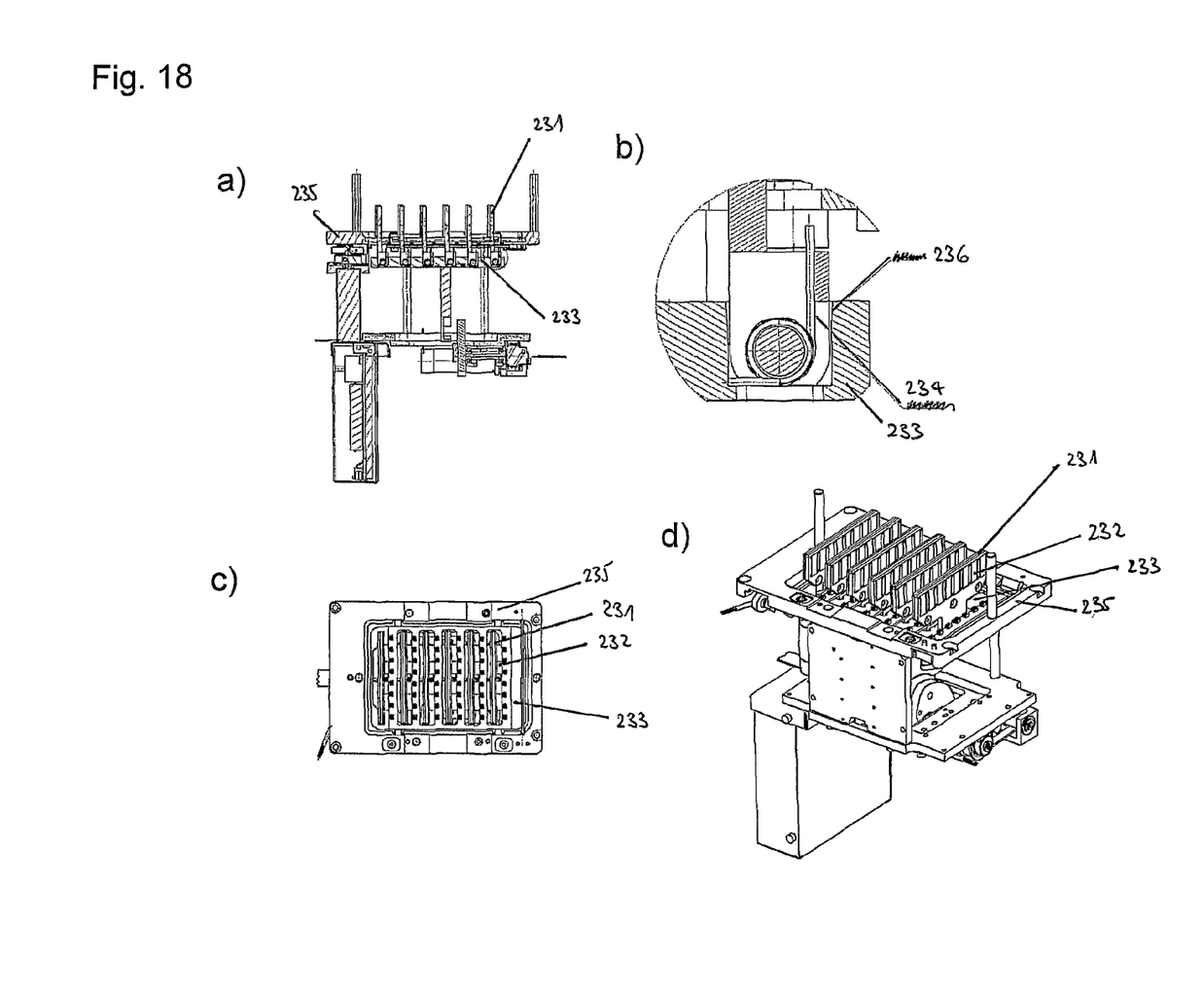

A spring is attached to the base (233) of any one frame (231) 18 a), b)). The spring presses the magnets (232) against the vessels (103). This ensures a contact between magnets (232) and vessels (103) during magnetic separation. Preferably, the magnet (232) contacts the vessel (103) on the side wall (109) located underneath the inlet (105). This has the advantage that liquid which is added by pipetting flows over the sequestered magnetic particles and ensures that particles are resuspended and that all samples in all vessels are treated identically.

This embodiment is particularly suited to separate a liquid (215) comprised in a multiwell plate (101) as hereinbefore described, from magnetic particles (216) when different levels of liquid (215) are contained in the vessels (103) of said multiwell plate (101).

While the invention has been described in detail with reference to specific examples, it will be apparent to one skilled in the art that various modifications can be made within the scope of this invention. Thus the scope of the invention should not be limited by the examples described herein, but by the claims presented below.

We claim:

1. A method of surveilling mixing and separation of a suspension comprising solid phase particles, comprising the steps of
    mixing or separating a suspension comprising solid phase particles from a liquid in a vessel, wherein said vessel comprises an open top end and a closed bottom;
    illuminating said vessel with a light source;
    detecting light illuminated by said light source with a detecting device, wherein said detecting device is positioned above said vessel;
    using measurement of light detected by said detecting device, using a control unit for calculating particle distribution of said solid phase particles present in said liquid,
wherein for surveiling of mixing, the control unit is programmed to identify vessels as invalid wherein the detected light is above a certain predefined threshold indicating that the particle distribution is insufficient, and
wherein for surveiling of separation, the control unit is programmed to identify vessels as invalid wherein the detected light is below a certain predefined threshold indicating that the particle separation is insufficient.

2. The method of claim 1, wherein said particles are magnetic or magnetizable particles and wherein said method additionally comprises the step of removing said pipette tips from said vessel following mixing.

3. The method of claim 1, wherein said mixing comprises aspirating and dispensing with a pipette tip and wherein said method additionally comprises the step of removing said pipette tips from said vessel following mixing.

4. The method of claim 1, wherein said separating comprises exposing said vessel to a magnetic field.

5. The method according to claim 1, wherein said light source is located below said vessel.

6. The method of claim 1, wherein said detecting device is mounted on the side of said pipetting unit.

7. The method according to claim 1, wherein said detecting comprises acquiring of images, and wherein said images are processed using a data reduction method, thereby obtaining reduced image data.

8. The method of claim 7, wherein said data reduction method comprises processing algorithms.

9. The method of claim 7, wherein a discriminating algorithm flags test results according to values of the reduced image data.

10. An analytical system comprising
    a separation device, wherein said separation device comprises a separation station comprising magnets which can be moved vertically, said separation station comprising light sources,
    at least one vessel, wherein said at least one vessel comprises an open top end and a closed bottom and wherein said at least one vessel comprises magnetic or magnetizable particles in a liquid; and wherein said light sources are located below said at least one vessel;
    a pipetting unit for aspirating and dispensing said magnetic particles in said liquid;
    a detecting device, located above said vessel when the pipette tip is moved away from the vessel, wherein said light sources illuminate said vessels;
    a control unit programmed to calculate particle distribution of said magnetic particles in said liquid using measurement of light by said detecting device and for surveiling of mixing, to identify vessels as invalid wherein the detected light is above a certain predefined threshold indicating that the particle distribution is insufficient, and for surveiling of separation, to identify vessels as invalid wherein the detected light is below a certain predefined threshold indicating that the particle separation is insufficient.

11. The analytical system of claim 10, wherein said detecting device is mounted on the side of said pipetting unit.

12. The analytical system according to claim 10, wherein said at least one vessels are comprised in a multiwell plate.

13. The analytical system according to claim 12, wherein one of said light sources is located below any one of said vessels of said multiwell plate.

14. The analytical system of claim 10, wherein said detection device is a CCD.

* * * * *